US012697363B2

(12) United States Patent     (10) Patent No.: US 12,697,363 B2

Chen et al.     (45) Date of Patent: Aug. 4, 2026

(54) COMPOSITION FOR INHIBITING DIABETES MELLITUS AND METHOD OF MANUFACTURING THE SAME

(71) Applicant: Forte Capital Ltd., Taipei City (TW)

(72) Inventors: Bing-Huei Chen, Taipei City (TW); Yu-Chi Huang, Taipei City (TW); Yung-Sheng Chang, Taipei City (TW); Tai-Yi He, Taipei City (TW)

(73) Assignee: Forte Capital Ltd., Taipei (TW)

( * ) Notice: Subject to any disclaimer, the term of this patent is extended or adjusted under 35 U.S.C. 154(b) by 395 days.

(21) Appl. No.: 18/359,636

(22) Filed: Jul. 26, 2023

(65) Prior Publication Data

US 2024/0033313 A1     Feb. 1, 2024

(30) Foreign Application Priority Data

Jul. 26, 2022 (TW) .................................. 111128028
Dec. 7, 2022 (TW) .................................. 111147051

(51) Int. Cl.
| | |
|---|---|
| *A61K 36/00* | (2006.01) |
| *A61K 9/107* | (2006.01) |
| *A61K 31/05* | (2006.01) |
| *A61K 31/08* | (2006.01) |
| *A61K 31/11* | (2006.01) |
| *A61K 31/192* | (2006.01) |
| *A61K 31/216* | (2006.01) |
| *A61K 31/343* | (2006.01) |
| *A61K 31/685* | (2006.01) |
| *A61K 31/7048* | (2006.01) |
| *A61K 36/48* | (2006.01) |
| *A61K 36/54* | (2006.01) |
| *A61P 3/10* | (2006.01) |
| *B82Y 5/00* | (2011.01) |

(52) U.S. Cl.
CPC ............ *A61K 36/54* (2013.01); *A61K 9/1075* (2013.01); *A61K 31/05* (2013.01); *A61K 31/08* (2013.01); *A61K 31/11* (2013.01); *A61K 31/192* (2013.01); *A61K 31/216* (2013.01); *A61K 31/343* (2013.01); *A61K 31/685* (2013.01); *A61K 31/7048* (2013.01); *A61K 36/48* (2013.01); *A61P 3/10* (2018.01); *A61K 2236/33* (2013.01); *B82Y 5/00* (2013.01)

(58) Field of Classification Search
CPC ...................................................... A61K 36/54
See application file for complete search history.

*Primary Examiner* — Qiuwen Mi

(74) *Attorney, Agent, or Firm* — MUNCY, GEISSLER, OLDS & LOWE, P.C.

(57) ABSTRACT

A composition for inhibiting diabetes mellitus comprising 1 part by weight of soybean oil, 5 to 14 parts by weight of emulsifier, 0.5 to 2 parts by weight of lecithin, 0.3 to 2 parts by weight of PEG, 81 to 91 parts by weight of deionized water and 2.345 to 17.833 parts by weight of cinnamalde-hyde. Furthermore, the present invention also provides a method for manufacturing the composition for inhibiting diabetes mellitus, to produce the aforementioned composition for inhibiting diabetes mellitus.

10 Claims, 1 Drawing Sheet

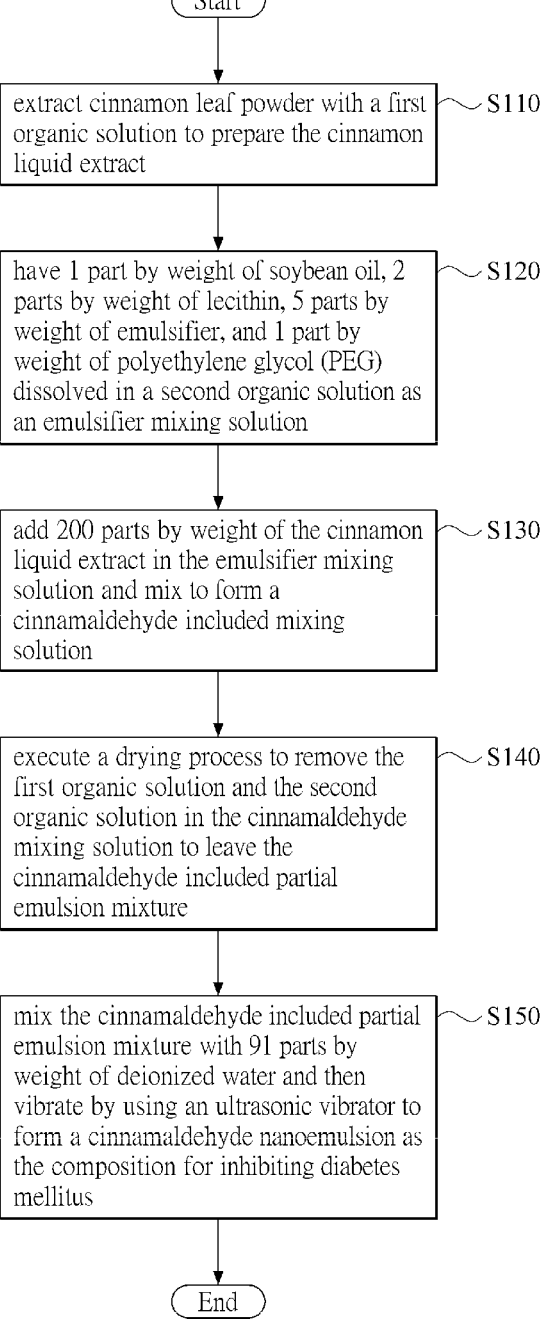

Start extract cinnamon leaf powder with a first organic solution to prepare the cinnamon liquid extract ~ S110 have 1 part by weight of soybean oil, 2 parts by weight of lecithin, 5 parts by weight of emulsifier, and 1 part by weight of polyethylene glycol (PEG) dissolved in a second organic solution as an emulsifier mixing solution ~ S120 add 200 parts by weight of the cinnamon liquid extract in the emulsifier mixing solution and mix to form a cinnamaldehyde included mixing solution ~ S130 execute a drying process to remove the first organic solution and the second organic solution in the cinnamaldehyde mixing solution to leave the cinnamaldehyde included partial emulsion mixture ~ S140 mix the cinnamaldehyde included partial emulsion mixture with 91 parts by weight of deionized water and then vibrate by using an ultrasonic vibrator to form a cinnamaldehyde nanoemulsion as the composition for inhibiting diabetes mellitus ~ S150

End

COMPOSITION FOR INHIBITING DIABETES MELLITUS AND METHOD OF MANUFACTURING THE SAME

This application claims the benefit of Taiwan Patent Application Serial No. 111128028, filed Jul. 26, 2022 and Serial No. 111147051, filed Dec. 7, 2022, the subject matter of which is incorporated herein by reference.

BACKGROUND OF THE INVENTION

Field of the Invention

The present invention is related to a composition for inhibiting diabetes mellitus and a method of manufacturing the same, and more particularly is related to a composition including extracts of cinnamon leaf for inhibiting Parkinson's disease and a method of manufacturing the same.

Description of the Related Art

In recent years, because of the vigorous development of technology, grain production is growing, and food processing technology is in constant progress, such that food production cost can be effectively reduced to have people capable of buying more food at low price. Because it is easy to access to food, more and more people consume excessive food more than they need and even form the bad habit of eating too much overtime. In addition, because most of the processed food is too delicate or contains too much fat, it would be easy to become obesity and cause diabetes mellitus.

General speaking, diabetes mellitus caused by obesity is primary the type 2 diabetes mellitus characterized with insulin secretion problem, such diabetes mellitus is a metabolic disease, which may cause many complications without adequate treatment or diet control.

The treatment for diabetes mellitus in present is to inject insulin directly for allowing the broken-down glucose in blood entering cells or use oral hypoglycemic drugs to stimulate pancreas secreting insulin to achieve the object of lowering blood sugar.

As mentioned above, the oral hypoglycemic drugs in present can be roughly divided into the classes of sulfonylureas, meglitinide, biguanides, $\alpha$-glucose inhibitors, and insulin sensitizers, etc. However, most of the drugs have some side effects, for example, sulfonylureas class and meglitinide class compounds may cause low blood sugar, biguanides class compound and $\alpha$-glucose inhibitors may cause abdominal discomfort such as abdominal bloating or diarrhea, and insulin sensitizers may cause the problems of weight gains, edema, diarrhea, or headache, and in some cases even cause hepatotoxicity.

In the present technology, research has indicated that eating cinnamon powder may have a lower fasting plasma glucose, some further research found that this is primary because cinnamaldehyde in the cinnamon powder is helpful for accelerating insulin release and improving insulin sensitivity such that the effect of blood-sugar control can be enhanced to inhibit diabetes mellitus effectively. In addition, cinnamaldehyde also has the functions of anti-inflammatory and antioxidation, etc.

Although cinnamaldehyde is helpful for inhibiting diabetes mellitus, the common way to take cinnamaldehyde is to eat cinnamon powder directly, at most processing cinnamon leaves into cinnamon hydrosol or cinnamon liquid extract. Although cinnamon hydrosol or cinnamon liquid extract may achieve better absorption then eating cinnamon powder directly, but the enhancement is limited. In addition, there has very few research in practice focusing on how to enhance absorption of effective contents in cinnamon leaves, thus, there exists a need to do the research regarding how to enhance absorption of effective contents in cinnamon leaves.

BRIEF SUMMARY OF THE INVENTION

In view of the prior art, most of the existed oral medications for diabetes mellitus have some side effects, which would cause a greater burden for diabetes mellitus patients with poor health. Although it is known that cinnamon powder produced by grinding cinnamon leaves have significant inhibition to diabetes mellitus, and some research indicates that this is because cinnamon leaf contains plenty of cinnamaldehyde, but there has no research focusing on how to enhance absorption of effective contents in cinnamon leaf. Accordingly, it is a main object of the present invention to provide a composition for inhibiting diabetes mellitus and manufacturing method thereof, which is capable to produce a composition containing cinnamaldehyde through a simple process and a specific composition ratio from a natural source, to make cinnamaldehyde absorbed more easily.

In order to resolve the problem of prior art, the disclosure provides a composition for inhibiting diabetes mellitus. The composition for inhibiting diabetes mellitus comprises 1 part by weight of soybean oil, 5 to 14 parts by weight of emulsifier, 0.5 to 2 parts by weight of lecithin, 0.3 to 2 parts by weight of polyethylene glycol (PEG), 81 to 91 parts by weight of deionized water, and 2.345 to 17.833 parts by weight of cinnamaldehyde, wherein an average particle size of the composition for inhibiting diabetes mellitus is ranged between 33 nm to 37 nm, and a polydispersity index of the composition for inhibiting diabetes mellitus is ranged between 012 to 0.20.

In accordance with an embodiment of the present disclosure, the composition for inhibiting diabetes mellitus further comprises 0.14734 to 0.8813 parts by weight of cinnamic acid.

In accordance with an embodiment of the present disclosure, the composition for inhibiting diabetes mellitus further comprises 0.04122 to 0.4334 parts by weight of cinnamyl alcohol.

In accordance with an embodiment of the present disclosure, the composition for inhibiting diabetes mellitus further comprises 0.02504 to 0.0833 parts by weight of kaempferol.

In accordance with an embodiment of the present disclosure, the composition for inhibiting diabetes mellitus further comprises 0.0177 to 0.0947 parts by weight of benzoic acid.

In accordance with an embodiment of the present disclosure, the composition for inhibiting diabetes mellitus further comprises 0.0102 to 0.156 parts by weight of eugenol.

In accordance with an embodiment of the present disclosure, the composition for inhibiting diabetes mellitus further comprises 0.0037 to 0.0093 parts by weight of quercetin.

In accordance with an embodiment of the present disclosure, the composition for inhibiting diabetes mellitus further comprises 0.02504 to 0.0833 parts by weight of kaempferol-3-$\beta$-D-glucopyranoside.

In accordance with an embodiment of the present disclosure, the composition for inhibiting diabetes mellitus further comprises 0.0011 to 0.0067 parts by weight of rutin.

In accordance with an embodiment of the present disclosure, the composition for inhibiting diabetes mellitus further comprises 0.00108 to 0.00521 parts by weight of caffeic acid, 0.00086 to 0.0012 parts by weight of coumarin, 0.00038 to 0.0014 parts by weight of hyperoside and iso-quercetin, 0.00080 to 0.001 parts by weight of p-coumaric acid, and 0.00012 to 0.0015 parts by weight of neochloro-genic acid.

In addition, a method of manufacturing the composition for inhibiting diabetes mellitus as mentioned above is also provided. The method comprises the following steps (A) to (E).

Firstly, step (A) is to prepare a cinnamon liquid extract, wherein the cinnamon liquid extract comprises a first organic solution and at least one solute totally dissolved in the first organic solution, wherein the at least one solute comprises 90% to 99% by weight of cinnamaldehyde.

Then, step (B) is to have 1 part by weight of soybean oil, 2 parts by weight of lecithin, 5 parts by weight of emulsifier, and 1 part by weight of polyethylene glycol (PEG) dissolved in a second organic solution as an emulsifier mixing solution, wherein the first organic solution and the second organic solution are ethanol solutions.

Thereafter, step (C) is to add 200 parts by weight of the cinnamon liquid extract in the emulsifier mixing solution and mixing to form a cinnamaldehyde added mixing solution, wherein the cinnamaldehyde added mixing solution comprises the first organic solution and the second organic solution, wherein the cinnamaldehyde, the soybean oil, and the lecithin in the cinnamaldehyde add mixing solution are miscible with each other to form a cinnamaldehyde added oil, and the cinnamaldehyde added oil and the emulsifier are partially bonded to form a cinnamaldehyde added partial emulsion mixture.

Then, step (D) is to execute a drying process to remove the first organic solution and the second organic solution in the cinnamaldehyde mixing solution to leave the cinnamal-dehyde added partial emulsion mixture.

Finally, step (E) is to mix the cinnamaldehyde included partial emulsion mixture with 91 parts by weight of deion-ized water to form a cinnamaldehyde nanoemulsion as the composition for inhibiting diabetes mellitus.

In accordance with an embodiment of the present disclo-sure, the step (E) is to mix the cinnamaldehyde included partial emulsion mixture with 91 parts by weight of the deionized water and then vibrate by using an ultrasonic vibrator to form the cinnamaldehyde nanoemulsion.

In accordance with an embodiment of the present disclo-sure, a concentration of the ethanol solution is higher than 80%.

In accordance with an embodiment of the present disclo-sure, the step (A) is to extract cinnamon leaf powder with the first organic solution to prepare the cinnamon liquid extract. Preferably, a weight ratio of the cinnamon leaf powder and the first organic solution is 1:5.

As described, it is proved though experiments that cin-namaldehyde nanoemulsion produced by the present inven-tion is more effective for inhibiting Parkinson's disease than the existed cinnamon liquid extract or Indigenous cinnamon hydrosol, and thus is able to be used as the composition for inhibiting diabetes mellitus.

Further features of the present invention would be described in the following embodiments and FIGURE.

BRIEF DESCRIPTION OF THE DRAWINGS

The sole FIGURE is a flow chart showing the method of manufacturing a composition for inhibiting diabetes mellitus in accordance with a preferred embodiment of the present invention.

4

DETAILED DESCRIPTION OF THE
EMBODIMENTS

Specific implementations of this disclosure are further described in detail below with reference to the accompany-ing drawings. According to the following descriptions and claims, the advantages and features of this disclosure are clearer. It should be noted that the drawings are drawn by using an extremely simplified form and imprecise propor-tion, which are only used for conveniently and clearly assisting in explaining the objective of the embodiments of this disclosure.

In accordance with a preferred embodiment of the present invention, a composition for inhibiting Parkinson's disease which mainly contains soybean oil, emulsifier, lecithin, PEG, deionized water, and cinnamaldehyde is provided. The composition for inhibiting Parkinson's disease provided in the present embodiment is to produce cinnamaldehyde nano particles by using soybean oil, emulsifier, lecithin, PEG, and deionized water to improve body absorption so as to enhance efficacy of cinnamaldehyde for inhibiting diabetes mellitus.

Please refer to the sole FIGURE, wherein the sole FIG-URE is a flow chart showing the method of manufacturing a composition for inhibiting diabetes mellitus in accordance with a preferred embodiment of the present invention. As shown, the method of manufacturing the composition for inhibiting diabetes mellitus comprises the following steps S110 to S150.

Firstly, step S110 is to extract cinnamon leaf powder with a first organic solution to prepare the cinnamon liquid extract, wherein, a weight ratio of the cinnamon leaf powder and the first organic solution is 1:5 for example. The cinnamon liquid extract comprises a first organic solution and at least one solute totally dissolved in the first organic solution.

In the present embodiment, the first organic solution is an ethanol solution with a concentration higher than 80%, and the solute comprises 90 wt % to 99 wt % of cinnamaldehyde. However, the present invention is not restricted thereto. The other organic solutions capable of extracting cinnamalde-hyde can be used as the first organic solution.

As mentioned above, the solute is the substance of the ingredients of the cinnamon leaf powder capable to be extracted by the first organic solution. The percentage of cinnamaldehyde contained in the solute mainly depends on the factors such as growing conditions and species of the cinnamon leaf powder. However, the present invention is not restricted thereto. In addition to cinnamaldehyde, the solute may contain other substances such as cinnamyl alcohol. In addition, the species of the cinnamon leaf powder can be Indigenous cinnamon, Cinnamomum zeylanicum, or Cinna-momum cassia, etc.

Then, step S120 is to have 1 part by weight of soybean oil, 2 parts by weight of lecithin, 5 parts by weight of emulsifier, and 1 part by weight of polyethylene glycol (PEG) dissolved in a second organic solution as an emulsifier mixing solu-tion, wherein the emulsifier can be Tween 80 (CAS No. 9005-65-6) for example, but the present invention is not restricted thereto, the other emulsifiers commonly used in food industry can be used. In addition, in the present embodiment, the second organic solution is also an ethanol solution, and a concentration of the ethanol solution is higher than 80%.

Afterward, step S130 is to add 200 parts by weight of the cinnamon liquid extract in the emulsifier mixing solution and mix to form a cinnamaldehyde included mixing solution. Because the solvent of the cinnamon liquid extract is the first organic solution and the solvent of the emulsifier mixing solution is the second solution, the cinnamaldehyde included mixing solution comprises the first organic solution and the second organic solution.

In the aforementioned cinnamaldehyde included mixing solution, cinnamaldehyde, soybean oil, and lecithin are miscible with each other to form a cinnamaldehyde included oil, and the cinnamaldehyde included oil and the emulsifier are partially bonded to form a cinnamaldehyde included partial emulsion mixture.

Thereafter, step S140 is to execute a drying process to remove the first organic solution and the second organic solution in the cinnamaldehyde mixing solution to leave the cinnamaldehyde included partial emulsion mixture. For example, the drying process is carried out by reducing pressure to lower the boiling point of the first organic solution and the second organic solution, so as to accelerate the volatilization of the first organic solution and the second organic solution to leave the cinnamaldehyde included partial emulsion mixture. Moreover, in the drying process, other than the way of reducing pressure, nitrogen gas can be used for blowing to the remained first organic solution and the second organic solution after most of the first organic solution and the second organic solution are volatilized, so as to make sure that the first organic solution and the second organic solution are totally volatilized to leave the cinnamaldehyde included partial emulsion mixture.

Finally, step S150 is to mix the cinnamaldehyde included partial emulsion mixture with 91 parts by weight of deionized water and then vibrate by using an ultrasonic vibrator to form a cinnamaldehyde nanoemulsion as the composition for inhibiting diabetes mellitus.

In accordance with the aforementioned method of manufacturing the composition for inhibiting diabetes mellitus, for example, when preparing the cinnamon liquid extract in step S110, if 500 g of cinnamon leaf powder is added in 2500 ml of 80% ethanol solution (the first organic solution), extracted by using ultrasonic vibration at a temperature of 60° C. for 2 hours, and filtered with filter paper in the suction filtration process to collect the supernatant liquid, about 2000 ml of cinnamon liquid extract with 5000 ppm cinnamaldehyde. Thus, it can be found that the cinnamon leaf powder used in the present embodiment contains about 2 wt % of cinnamaldehyde. That is, the cinnamon leaf powder contains about 98 wt % carbohydrate and the other ingredients (including the solutes dissoluble in the first organic solution).

As mentioned above, in step S120, each part by weight can be 0.1 g for example. That is, 0.1 g of soybean oil, 0.2 g of lecithin and 0.5 g of Tween 80 (the emulsifier), and 0.1 g of polyethylene glycol (PEG) are dissolved in 100 ml of 99% ethanol solution (the second organic solution) to provide the emulsifier mixing solution.

Then, because in the aforementioned step S120, each part by weight is 0.1 g, step S130 is to add 20 g of cinnamon liquid extract in the emulsifier mixing solution and mix to form a cinnamaldehyde included mixing solution, wherein because the cinnamon liquid extract contains 5000 ppm cinnamaldehyde, the density thereof would be slightly increased and close to 1 g/ml. In practice, using 20 g of cinnamon liquid extract in the emulsifier mixing solution is for the purpose of convenience.

Next, because step S140 to execute a drying process to remove the first organic solution and the second organic solution in the cinnamaldehyde mixing solution to leave the cinnamaldehyde included partial emulsion mixture, it is only needed to use the amount of the first organic solution and the second organic solution used in the steps S110 to S130 sufficient to execute the steps S110 to S130. In detail, in step S110, it is only needed to use the amount of the first organic solution sufficient to extract cinnamaldehyde from the cinnamon leaf powder, and the ratio of the first organic solution and the cinnamon leaf powder only affects the concentration of cinnamaldehyde in the cinnamon liquid extract. In step S120, it is only needed to use the amount of the second organic solution sufficient to dissolve soybean oil, lecithin, and emulsifier.

After removing the first organic solution and the second organic solution from the cinnamaldehyde included mixing solution, the cinnamaldehyde included partial emulsion mixture would be left naturally. Thereby, when the cinnamaldehyde included partial emulsion mixture is mixed with 91 parts by weight of deionized water in step S150 and then vibrate by using the ultrasonic vibrator for 1 hour, emulsifier in the cinnamaldehyde included partial emulsion mixture would be bonded to the water molecules effectively, so as to have the cinnamaldehyde included oil uniformly distributed in the deionized water with the help of the emulsifier to show the emulsion state. Thus, cinnamaldehyde included in the cinnamaldehyde included oil is in the condition of being dissolved in the oil and uniformly distributed in the deionized water so as to prevent aggregation of cinnamaldehyde to have cinnamaldehyde kept as individual molecules.

It should be noted that because the present embodiment has 1 part of PEG, which is a biocompatible polymer, dissolved in the second organic solution, the active ingredient (cinnamaldehyde) hard to dissolved in water can be dissolved in soybean oil and lecithin first, thereby when the deionized water is mixed with the cinnamaldehyde included partial emulsion mixture, cinnamaldehyde can be re-distributed from the oil state to the liquid state.

Although in the aforementioned embodiment, soybean oil, emulsifier, lecithin, PEG, and deionized water of the composition for inhibiting diabetes mellitus is provided at a weight ratio of 1:5:2:1:91 to produce cinnamaldehyde nanoemulsion, the detected composition ratio of the produced cinnamaldehyde nanoemulsion might be somewhat fluctuated. For example, take 1 part by weight of soybean oil as a reference, emulsifier might be ranged between 5 to 14 parts by weight, lecithin might be ranged between 0.5 to 2 parts by weight, PEG might be ranged between 0.3 to 2 parts by weight, and deionized water might be ranged between 81 to 91 parts by weight.

As mentioned above, based on 1 part by weight of soybean oil, after doing multigroup analysis to the compositions for inhibiting diabetes mellitus manufactured by using the aforementioned embodiment, an amount of cinnamaldehyde ranged between 2.345 to 17.833 parts by weight is detected and concentrated at the range between 8 to 12 parts by weight. Fluctuation of the amount of cinnamaldehyde is mainly due to the particle size of the cinnamon leaf powder in the beginning and the extracting process, but all the cinnamaldehyde in the composition can be nano emulsified through the aforementioned process and the reactions with other ingredients.

In addition, also based on 1 part by weight of soybean oil, after doing multigroup analysis to the compositions for inhibiting Parkinson's disease manufactured by using the aforementioned embodiment, 0.14734 to 0.8813 parts by weight of cinnamic acid, 0.04122 to 0.4334 parts by weight of cinnamyl alcohol, to 0.0833 parts by weight of kaempferol, 0.0177 to 0.0947 parts by weight of benzoic acid, 0.0102 to 0.156 parts by weight of eugenol, 0.0037 to 0.0093 parts by weight of quercetin, 0.02504 to 0.0833 parts by weight of kaempferol-3-β-D-glucopyranoside, 0.0011 to 0.0067 parts by weight of rutin, 0.00108 to 0.00521 parts by weight of caffeic acid, 0.00086 to 0.0012 parts by weight of coumarin, to 0.0014 parts by weight of hyperoside and isoquercetin, 0.00080 to 0.001 parts by weight of p-coumaric acid, and 0.00012 to 0.0015 parts by weight of neochlorogenic acid are detected. These ingredients are extracted together with cinnamaldehyde from cinnamon leaves. In practice, these minor ingredients are also contained in cinnamon leaves which have been used in the research to prove the effectiveness for inhibiting diabetes mellitus, thus, these ingredients are also helpful for inhibiting diabetes mellitus.

In order to FIGURE out the nano-scale characteristics of the cinnamaldehyde nanoemulsion, the present embodiment executes particle size distribution analysis, zeta-potential analysis, micrographic analysis, and stability analysis for the cinnamaldehyde nanoemulsion.

Firstly, particle size distribution analysis is executed by using dynamic light scattering. When light passes through the cinnamaldehyde nanoemulsion and reaches the cinnamaldehyde particles, the light is scattered by the cinnamaldehyde particles. Because the cinnamaldehyde particles have Brownian motion in the solution, light intensity would be changed. In addition, because larger particles move slower than smaller one in the solution, particle size of cinnamaldehyde particles can be determined through the detection of light intensity change at a certain angle. Through the detection by using dynamic light scattering, the cinnamaldehyde nanoemulsion has an average particle size ranged between 33 nm to 37 nm and a polydispersity index (PDI) ranged between 0.12 to 0.20.

As mentioned above, PDI is a molecular weight distribution index, which is used to represent variation of molecular weight of polymer as an index for estimating particle size uniformity of polymer. The lower index value means particle size distribution is more uniform. General speaking, PDI value ranges between 0.1-0.3 means uniform particle size distribution, which is also indicated as narrow size distribution, PDI value over 0.5 means non-uniform particle size distribution, which is also indicated as broad size distribution. Based on the aforementioned particle size distribution analysis, it is noted that particle size of the cinnamaldehyde nanoemulsion of the present embodiment shows a single group distribution.

Furthermore, zeta-potential analysis is an important index for evaluating cinnamaldehyde nanoemulsion stability. Zeta-potential is caused by the electrical charge due to dissociation, replacement, and adsorption of the groups on the particle surface. The higher zeta-potential indicates a stronger electrostatic repulsion to avoid particle aggregation, and thus represents higher stability. On the contrary, the lower zeta-potential indicates that individual particles would be aggregated easily to cause precipitation, and thus represents lower stability. Generally, 30 mV is used as the estimation value for zeta-potential, a zeta-potential value more than 30 mV or less than −30 mV indicates the solution has better stability, a zeta-potential value less than 30 mV or more than −30 mV indicates the solution has poor stability and the particles would be aggregated easily to cause precipitation. The zeta-potential value found in the cinnamaldehyde nanoemulsion of the present embodiment is −41.9 mV, which is less than −30 mV indicating that the cinnamaldehyde nanoemulsion is quite stable.

Micrographic analysis is carried out by negative staining the cinnamaldehyde nanoemulsion with phosphotungstic acid first and then observing size and types of the nano particles by using transmission electron microscope (TEM). The observation shows that the cinnamaldehyde nanoemulsion has a uniform particle size distribution, and no aggregation is found. After scale conversion, the average particle size is about 37.36 nm, which is close to the average particle size of 36.58 nm detected by using dynamic light scattering.

Stability analysis is to check the change of average particle size, polydispersity index, and zeta-potential after the cinnamaldehyde nanoemulsion stored at 4° C. for 90 days, which are shown in the following table 1.

TABLE 1

| Time (days) | Average particle size (nm) | Polydispersity index | Zeta-potentia (mV) |
|---|---|---|---|
| 1 | 36.58 | 0.180 ± 0.01 | −46.13 ± 0.34 |
| 7 | 35.37 | 0.129 ± 0.05 | −39.83 ± 0.12 |
| 14 | 35.02 | 0.172 ± 0.00 | −36.40 ± 0.99 |
| 21 | 35.76 | 0.157 ± 0.02 | −41.10 ± 0.93 |
| 30 | 33.58 | 0.164 ± 0.01 | −37.90 ± 0.94 |
| 60 | 35.95 | 0.202 ± 0.01 | −39.40 ± 0.88 |
| 90 | 34.89 | 0.135 ± 0.06 | −39.50 ± 0.22 |

As described in table 1, the cinnamaldehyde nanoemulsion is stored at 4° C. and sampled with certain time intervals to observe the changes of particle size and zeta-potential. The observation shows that there has no significant change regarding average particle size, polydispersity index, and zeta-potential, which indicates that cinnamaldehyde nanoemulsion stored at 4° C. has good stability. In addition, according to the analysis result shown in Table 1, the cinnamaldehyde nanoemulsion (i.e., the composition for inhibiting diabetes mellitus of the present invention) provided in the present embodiment features an average particle size ranged between 33 nm to 37 nm and a PDI index ranged between 0.12 to 0.20, does have cinnamaldehyde showing the state of nanoemulsion, which is helpful for body absorption.

In addition, in order to check the efficacy of the cinnamaldehyde nanoemulsion used as the composition for inhibiting diabetes mellitus, the following animal test is executed for testing the cinnamaldehyde nanoemulsion.

It is noted first that the test object of the present experiments is the mouse with high fat diet and type 2 diabetes mellitus induced by streptozotocin (STZ) and nicotinamide (NA). In general, as the disease gets worse, the symptoms of eat more, drink more, polyuria, and weight loss would be more significant.

As mentioned above, the experiments have the mice divided into the following experimental groups:

1. Normal control group (NC): mice without diabetes mellitus induction;
2. Diabetes mellitus induced group (DC): mice with diabetes mellitus induction;
3. Indigenous cinnamon powder hydrosol group (HP): mice with diabetes mellitus fed with indigenous cinnamon powder dissolved in hydrosol (0.5 g powders dissolved in 10 ml cinnamon leaf distillate) (10 mL/kg);
4. Low dosage cinnamon liquid extract group (EL): mice with diabetes mellitus fed with low dosage of cinnamon liquid extract (20 mg/kg) dissolved in water (similar to the mice with diabetes mellitus induction of group 2);

5. Low dosage cinnamaldehyde nanoemulsion group (NL): mice with diabetes mellitus fed with low dosage of cinnamaldehyde nanoemulsion (20 mg/kg);

6. High dosage cinnamon liquid extract group (EH): mice with diabetes mellitus fed with high dosage of cinnamon liquid extract (60 mg/kg) dissolved in water; and 7. High dosage cinnamaldehyde nanoemulsion group (NH): mice with diabetes mellitus fed with high dosage of cinnamaldehyde nanoemulsion (60 mg/kg).

Please refer to the following table 2, wherein table 2 shows change of body weight of the mice.

TABLE 2

| | Body weight of mice (g/rat) | | | | |
| --- | --- | --- | --- | --- | --- |
| Group | Week 0 | Week 1 | Week 2 | Week 3 | Week 4 |
| NC | 215.00 | 263.33 | 315.00 | 355.00 | 406.67 |
| DC | 211.67 | 240.00 | 291.67 | 325.00 | 326.67 |
| HP | 213.33 | 241.67 | 298.33 | 361.67 | 375.00 |
| EL | 212.50 | 246.67 | 308.33 | 368.33 | 368.33 |
| NL | 220.00 | 248.33 | 316.67 | 371.67 | 403.33 |
| EH | 220.00 | 246.67 | 320.00 | 376.67 | 411.67 |
| NH | 211.67 | 245.00 | 320.00 | 376.67 | 428.33 |

As shown in table 2, at week 0, there has no significant difference among body weight of each of the groups ($p > 0.05$); at feeding week 1, after inducing type 2 diabetes mellitus with streptozotocin (STZ) together with nicotinamide (NA), body weight of the mice of the groups with type 2 diabetes mellitus induction (DC, HP, EL, NL, EH, NH) is significantly lower than the normal control group (NC) ($p < 0.05$); at feeding week 4, body weight of the mice of diabetes mellitus induced group (DC) is significantly lower than the normal control group (NC) with an amount of 19.67%, but body weights of the other groups are significantly higher than the normal control group (NC) ($p < 0.05$). Body weights of indigenous cinnamon powder hydrosol group (HP), low dosage cinnamon liquid extract group (EL), low dosage cinnamaldehyde nanoemulsion group (NL), high dosage cinnamon liquid extract group (EH), and high dosage cinnamaldehyde nanoemulsion group (NH) are higher than diabetes mellitus induced group (DC) with the amounts of 14.79%、12.75%、23.47%、26.02% and 31.12% showing significant difference ($p < 0.05$), respectively, which indicates that all the groups either fed with cinnamon liquid extract or cinnamaldehyde nanoemulsion can relieve weight loss symptom of diabetes mellitus mice.

Please refer to the following table 3, wherein table 3 shows change of food intake of the mice.

TABLE 3

| | Food intake (g/day/rat) | | | | |
| --- | --- | --- | --- | --- | --- |
| Group | Week 0 | Week 1 | Week 2 | Week 3 | Week 4 |
| NC | 17.50 | 37.50 | 35.00 | 31.25 | 32.50 |
| DC | 18.75 | 30.00 | 22.50 | 31.25 | 32.50 |
| HP | 16.25 | 33.13 | 30.00 | 30.00 | 32.50 |
| EL | 15.63 | 21.25 | 20.00 | 32.50 | 33.75 |
| NL | 15.00 | 26.25 | 26.25 | 31.25 | 32.50 |
| EH | 17.50 | 21.25 | 22.50 | 22.50 | 27.50 |
| NH | 14.38 | 26.25 | 26.25 | 21.25 | 25.00 |

As shown in table 3, at week 0, there has no significant difference among food intake of each of the groups ($p > 0.05$). at feeding week 4, there has no significant difference between food intakes of the mice of diabetes mellitus induced group (DC) and the normal control group (NC)

($p > 0.05$), in compared with diabetes mellitus induced group (DC), food intakes of indigenous cinnamon powder hydrosol group (HP), low dosage cinnamon liquid extract group (EL) and low dosage cinnamaldehyde nanoemulsion group (NL) have no tendency of decreasing, high dosage cinnamon liquid extract group (EH) shows a tendency of decreasing with the amount of 15.38% but fails to reach significant difference ($p > 0.05$), high dosage cinnamaldehyde nanoemulsion group (NH) shows a tendency of decreasing with the amounts of 23.08% showing significant difference ($p < 0.05$) in compared with diabetes mellitus induced group (DC), which indicates that high dosage of cinnamaldehyde nanoemulsion is helpful for reducing feeling of hunger for the sick diabetes mellitus mice.

Please refer to the following table 4, wherein table 4 shows change of water intake of the mice.

TABLE 4

| | Water intake (g/day/rat) | | | | |
| --- | --- | --- | --- | --- | --- |
| Group | Week 0 | Week 1 | Week 2 | Week 3 | Week 4 |
| NC | 35.00 | 28.75 | 46.25 | 45.00 | 46.25 |
| DC | 31.25 | 25.00 | 38.75 | 63.75 | 72.50 |
| HP | 35.00 | 28.75 | 35.00 | 47.50 | 50.00 |
| EL | 37.50 | 30.00 | 45.00 | 60.00 | 63.75 |
| NL | 33.75 | 28.75 | 51.25 | 55.00 | 38.75 |
| EH | 35.00 | 18.75 | 43.75 | 37.50 | 37.50 |
| NH | 31.25 | 27.50 | 35.00 | 33.75 | 30.00 |

As shown in table 4, at week 0, there has no significant difference among water intake of each of the groups ($p > 0.05$). at feeding week 4, in compared with diabetes mellitus induced group (DC), water intakes of indigenous cinnamon powder hydrosol group (HP) and low dosage cinnamon liquid extract group (EL) shows a tendency of decreasing with the amounts of 31.03% and 12.07%, respectively, but fail to reach significant difference ($p > 0.05$), in compared with diabetes mellitus induced group (DC), water intakes of low dosage cinnamaldehyde nanoemulsion group (NL), high dosage cinnamon liquid extract group (EH), and high dosage cinnamaldehyde nanoemulsion group (NH) have a tendency of decreasing with the amounts of 46.55%, 48.28%, and 58.62% respectively showing significant difference ($p < 0.05$), which indicates that low dosage of cinnamaldehyde nanoemulsion, high dosage of cinnamon liquid extract, and high dosage of cinnamaldehyde nanoemulsion are helpful for reducing feeling of thirsty for the sick diabetes mellitus mice.

Please refer to the following table 5, wherein table 5 shows change of fasting plasma glucose of the mice.

TABLE 5

| | Fasting plasma glucose value of mice (mg/dL) | | | | |
| --- | --- | --- | --- | --- | --- |
| Group | Week 0 | Week 1 | Week 2 | Week 3 | Week 4 |
| NC | 103.33 | 98.67 | 103.83 | 107.33 | 106.17 |
| DC | 105.50 | 257.33 | 344.17 | 412.50 | 448.00 |
| HP | 103.00 | 274.00 | 309.67 | 366.00 | 352.17 |
| EL | 96.67 | 265.17 | 291.83 | 321.00 | 344.50 |
| NL | 101.50 | 288.50 | 300.17 | 318.00 | 295.67 |
| EH | 104.50 | 261.67 | 242.67 | 254.83 | 236.67 |
| NH | 101.17 | 262.83 | 297.50 | 239.33 | 205.17 |

As shown in table 5, at week 0 (day 1) fasting plasma glucose (FBG) values of each of the groups after fasted for 12 hours are less than the normal value of 126 mg/dL, which indicates that each mouse is healthy. After inducing diabetes mellitus at week 1 (from day 1 to day 7), FBG values of the mice are detected to be greater than 200 mg/dL, which indicates that diabetes mellitus is successfully induced in all the mice. In addition, at week 1, there has no significant difference among FBG values of the mice of each of the groups (p>0.05), which indicates that each group has similar severeness of inducing. After determining that diabetes mellitus is successfully induced in all the mice (day 7), the mice are fed with cinnamon liquid extract and high dosage cinnamaldehyde nanoemulsion for 4 weeks. At week 4, FBG value of diabetes mellitus induced group (DC) is significantly higher than the normal control group (NC), in compared with diabetes mellitus induced group (DC), FBG values of indigenous cinnamon powder hydrosol group (HP), low dosage cinnamon liquid extract group (EL), low dosage cinnamaldehyde nanoemulsion group (NL), high dosage cinnamon liquid extract group (EH), and high dosage cinnamaldehyde nanoemulsion group (NH) are significantly reduced with the amounts of 21.39%, 23.10%, 34.00%, 47.17%, and 54.20%, respectively, all of which have significant difference in compared with diabetes mellitus induced group (DC) (p>0.05), wherein the high dosage cinnamon liquid extract group (EH) and the high dosage cinnamaldehyde nanoemulsion group (NH) show a better effect for lowering blood sugar level, and the high dosage cinnamaldehyde nanoemulsion group (NH) has the best effect (54.20%).

Please refer to the following table 6 and table 7, wherein table 6 shows the result of glucose tolerance test of the mice, and table 7 shows change of insulin concentration and insulin resistance of the mice.

TABLE 6

| Group | Blood sugar value (mg/dl) | | | |
| | 0 min | 30 min | 60 min | 120 min |
|---|---|---|---|---|
| NC | 107.00 | 109.00 | 104.67 | 98.00 |
| DC | 434.33 | 590.50 | 591.83 | 584.83 |
| HP | 359.50 | 394.50 | 444.00 | 404.67 |
| EL | 320.33 | 399.50 | 444.17 | 424.50 |
| NL | 283.17 | 326.83 | 392.17 | 317.17 |
| EH | 244.33 | 300.50 | 311.17 | 264.67 |
| NH | 202.83 | 241.83 | 256.50 | 201.83 |

TABLE 7

| Group | Insulin concentration (µg/L) | HOMA-IR index |
|---|---|---|
| NC | 0.44 | 2.91 |
| RT | 0.90 | 24.24 |
| EH | 0.82 | 18.52 |
| EL | 0.77 | 14.99 |
| NH | 0.67 | 16.67 |
| NL | 0.61 | 9.05 |
| HP | 0.47 | 5.83 |

As shown in table 7, in compared with normal control group (NC), diabetes mellitus induced group (DC) has a significant higher insulin concentration (p<0.05), in compared with diabetes mellitus induced group (DC), insulin concentrations of indigenous cinnamon powder hydrosol group (HP), low dosage cinnamon liquid extract group (EL), and low dosage cinnamaldehyde nanoemulsion group (NL) have a tendency of decreasing with the amounts of 8.89%, 14.44%, and 25.56%, respectively, but fail to reach significant difference (p>0.05), and in compared with diabetes mellitus induced group (DC), insulin concentrations of high dosage cinnamon liquid extract group (EH) and high dosage cinnamaldehyde nanoemulsion group (NH) are reduced with the amounts of 32.22% and 47.78%, respectively, which have significant difference (p<0.05).

As mentioned above, in compared with normal control group (NC), insulin concentrations of diabetes mellitus induced group (DC), indigenous cinnamon powder hydrosol group (HP), and low dosage cinnamon liquid extract group (EL) are significantly increased (p<0.05); in compared with diabetes mellitus induced group (DC), insulin concentrations of high dosage cinnamon liquid extract group (EH) and high dosage cinnamaldehyde nanoemulsion group (NH) are significantly reduced and have no significantly difference in compared with normal control group (NC) (p>0.05), which indicates that high dosage cinnamon liquid extract and high dosage cinnamaldehyde nanoemulsion intake is helpful for inhibiting the condition of high insulin concentration in mice with diabetes mellitus, wherein the treatment of high dosage cinnamaldehyde nanoemulsion intake has the best effect (47.78%).

On the other hand, as shown in table 7, regarding homeostasis model assessment-insulin resistance (HOMA-IR) index, diabetes mellitus induced group (DC) has a significantly higher HOMA-IR index in compared with normal control group (NC) (p<0.05), in compared with diabetes mellitus induced group (DC), HOMA-IR index of indigenous cinnamon powder hydrosol group (HP) shows a tendency of decreasing with the amount of 23.60%, which fails to reach significant difference; in compared with diabetes mellitus induced group (DC), HOMA-IR indexes of low dosage cinnamon liquid extract group (EL), low dosage cinnamaldehyde nanoemulsion group (NL), high dosage cinnamon liquid extract group (EH), and high dosage cinnamaldehyde nanoemulsion group (NH) are reduced with the amounts of 38.16%, 31.23%, 62.67%, and 75.95% respectively, which have significant difference (p<0.05).

In addition, in compared with normal control group (NC), HOMA-IR indexes of diabetes mellitus induced group (DC) and indigenous cinnamon powder hydrosol group (HP) show a significant tendency of increasing (p<0.05); HOMA-IR indexes of low dosage cinnamon liquid extract group (EL) and low dosage cinnamaldehyde nanoemulsion group (NL) also show a significant tendency of increasing (p<0.05) in compared with normal control group (NC), but show a significant tendency of decreasing (p<0.05) in compared with diabetes mellitus induced group (DC); HOMA-IR indexes of high dosage cinnamon liquid extract group (EH) and high dosage cinnamaldehyde nanoemulsion group (NH) show a significant tendency of decreasing in compared with diabetes mellitus induced group (DC) (p<0.05), and have no significant difference in compared with normal control group (NC), which indicated that low dosage cinnamon liquid extract, low dosage cinnamaldehyde nanoemulsion, high dosage cinnamon liquid extract, and high dosage cinnamaldehyde nanoemulsion intakes may effectively reduce HOMA-IR index of diabetes mellitus mice, wherein high dosage cinnamon liquid extract and high dosage cinnamaldehyde nanoemulsion have a better effect, and high dosage cinnamaldehyde nanoemulsion has the best effect (75.95%).

Please refer to the following table 8, wherein table 8 shows the detection result of blood biochemical values of the mice.

TABLE 8

| | | | Blood biochemical values | | | | |
|---|---|---|---|---|---|---|---|
| Group | CHOL (mg/dl) | TRIC (mg/dl) | AST (U/L) | ALT (U/L) | URIC (mg/dl) | BUN (mg/dl) | CREA (mg/dl) |
| NC | 74.83 | 96.17 | 36.17 | 44.17 | 6.13 | 17.67 | 0.30 |
| DC | 96.17 | 178.50 | 84.67 | 80.00 | 8.10 | 32.33 | 0.58 |
| HP | 85.83 | 136.17 | 56.17 | 61.67 | 7.43 | 22.50 | 0.32 |
| EL | 77.33 | 130.67 | 45.83 | 56.00 | 7.25 | 21.00 | 0.52 |
| NL | 77.67 | 124.33 | 49.33 | 55.00 | 7.65 | 19.50 | 0.42 |
| EH | 68.00 | 105.00 | 45.67 | 35.17 | 8.02 | 16.50 | 0.36 |
| NH | 64.50 | 91.50 | 44.33 | 42.50 | 6.98 | 15.67 | 0.35 |

As shown in table 8, concentration of total cholesterol (CHOL) can be used for evaluating metabolic state of lipid, especially for those have high risk of coronary artery disease, and for evaluating risk of atherosclerosis together with concentration of other lipoproteins. Total cholesterol is composed of cholesterol-ester (about 70%) and free cholesterol (about 30%), which come from four lipoproteins including high-density lipoprotein (HDL), low-density lipoprotein (LDL), very-low-density lipoprotein (VLDL), and chylomicron. Thus, total cholesterol can be understood as the sum of cholesterol of the four lipoproteins. According to table 8, in compared with normal control group (NC), diabetes mellitus induced group (DC) has a significantly higher CHOL value ($p<0.05$); in compared with diabetes mellitus induced group (DC), CHOL values of indigenous cinnamon powder hydrosol group (HP), low dosage cinnamon liquid extract group (EL) and low dosage cinnamaldehyde nanoemulsion group (NL) have a tendency of decreasing with the amounts of 10.75%, 19.59%, and 19.24%, respectively, but fail to reach significant difference ($p>0.05$); in compared with diabetes mellitus induced group (DC), CHOL values of high dosage cinnamon liquid extract group (EH) and high dosage cinnamaldehyde nanoemulsion group (NH) are reduced with the amounts of 29.29% and 32.93% respectively, both of which have significant difference ($p<0.05$), which indicates that the groups fed with high dosage cinnamon liquid extract and high dosage cinnamaldehyde nanoemulsion may reduce the amount of CHOL in blood effectively.

Triglyceride (TG) can be used for evaluating metabolic state of lipid for the patients, especially those with high risk of secondary hyperlipidemia. High triglyceride may cause poor blood circulation, and also cause decreasing of concentration of HDL, which may greatly increase the possibility of getting vascular sclerosis. According to table 8, in compared with normal control group (NC), diabetes mellitus induced group (DC) has a significantly higher TG value ($p<0.05$); in compared with diabetes mellitus induced group (DC), TG values of indigenous cinnamon powder hydrosol group (HP), low dosage cinnamon liquid extract group (EL), low dosage cinnamaldehyde nanoemulsion group (NL), high dosage cinnamon liquid extract group (EH), and high dosage cinnamaldehyde nanoemulsion group (NH) have a tendency of decreasing with the amounts of 23.72%, 26.80%, 30.35%, 41.18%, and 48.74%, respectively, all of which have significant difference ($p<0.05$), which indicates that all the samples fed in the groups are effective for lowering TG value of blood, wherein the high dosage cinnamaldehyde nanoemulsion group (NH) has the most significant effect for lowering TG value.

Aspartate Aminotransferase (AST) is usually used for evaluating liver function, heart function, and muscle related diseases clinically. AST is an endo-enzyme related to amino acid metabolism. AST is abundant in liver and heart, muscle, kidneys and pancreas have mid-level AST, but there has little AST found in normal serum. AST would be found in serum only when the tissues of these parts are damaged. Base on the level of AST value, myocardial infarction, liver and gallbladder disease, and muscle disorder can be diagnosed. According to table 8, in compared with normal control group (NC), diabetes mellitus induced group (DC) has a significantly higher AST level ($p<0.05$); in compared with diabetes mellitus induced group (DC), AST level of indigenous cinnamon powder hydrosol group (HP) shows a tendency of decreasing with an amount of 33.66% but fails to reach significant difference ($p>0.05$); in compared with diabetes mellitus induced group (DC), AST levels of low dosage cinnamon liquid extract group (EL), low dosage cinnamaldehyde nanoemulsion group (NL), high dosage cinnamon liquid extract group (EH), and high dosage cinnamaldehyde nanoemulsion group (NH) have a tendency of decreasing with the amounts of 45.87%, 41.73%, 46.07%, and 47.64%, respectively, all of which have significant difference ($p<0.05$), which indicates that low dosage cinnamon liquid extract, low dosage cinnamaldehyde nanoemulsion, high dosage cinnamon liquid extract, and high dosage cinnamaldehyde nanoemulsion intakes are effective to reduce AST level in blood, so as to reduce liver damage for the sick diabetes mellitus mice.

Alanine aminotransferase (ALT) is usually used for evaluating the level of liver cell damage and classification of acute and chronic liver diseases clinically and is also an important index for evaluating treatment for liver disease. ALT is an endo-enzyme ALT related to amino acid metabolism. ALT is abundant in liver and kidneys, but heart and erythrocytes have a small amount of ALT. ALT activities in blood would be increased if the tissues of these parts, especially liver, are damaged. Base on the level of ALT value, myocardial infarction, liver and gallbladder disease, and muscle disorder can be diagnosed. According to table 8, in compared with normal control group (NC), diabetes mellitus induced group (DC) has a significantly higher ALT level ($p<0.05$); in compared with diabetes mellitus induced group (DC), ALT levels of indigenous cinnamon powder hydrosol group (HP), low dosage cinnamon liquid extract group (EL), low dosage cinnamaldehyde nanoemulsion group (NL), high dosage cinnamon liquid extract group (EH), and high dosage cinnamaldehyde nanoemulsion group (NH) have a tendency of decreasing with the amounts of 22.92%, 30.00%, 31.25%, 56.04%, and 46.88%, respectively, all of which have significant difference ($p<0.05$), which indicates that indigenous cinnamon powder hydrosol, low dosage cinnamon liquid extract, low dosage cinnamaldehyde nanoemulsion, high dosage cinnamon liquid extract, and high dosage cinnamaldehyde nanoemulsion intakes are effective to reduce ALT level in blood, so as to reduce liver damage for the sick diabetes mellitus mice.

Uric acid (Uric) is generally used in diagnoses and treatment tracking of gout, for evaluating kidney function, for evaluating possibility of happening of urinary tract stones together with uric acid concentration in urine, and for evaluating if there exist the risk of a large amount of tissue necrosis. Uric acid is a metabolic product of purine, the metabolism occurs in liver. Part of uric acid is excreted from urine, and part of uric acid is released to blood to cause gout. Gout, which is an inflammatory reaction caused by uric acid crystals. Concentration of uric acid in blood is related to metabolic function of kidneys, metabolic speed of purine, intake amount of high-purine food. Hyperuricemia is known as the condition when uric acid in blood is raised, uric acid may deposit in joints, soft tissues, etc., too much uric acid deposit in joints may cause joint inflammation called gout. According to table 8, in compared with normal control group (NC), diabetes mellitus induced group (DC) has a significantly higher Uric level (p<0.05); in compared with diabetes mellitus induced group (DC), Uric levels of indigenous cinnamon powder hydrosol group (HP), low dosage cinnamon liquid extract group (EL), low dosage cinnamaldehyde nanoemulsion group (NL), high dosage cinnamon liquid extract group (EH), and high dosage cinnamaldehyde nanoemulsion group (NH) have a tendency of decreasing with the amounts of 8.23%, 10.49%, 5.56%, 1.03%, and 13.79%, respectively, all of which fail to reach significant difference (p>0.05).

Blood urea nitrogen (BUN) is one of the commonly used indexes for evaluating kidney function. High concentration of BUN indicates that kidneys cannot effectively excrete urea nitrogen, and thus can be used for evaluating kidney diseases, such as impaired renal function, acute or chronic glomerulonephritis, nephrotic syndrome, etc. According to table 8, in compared with normal control group (NC), diabetes mellitus induced group (DC) has a significantly higher BUN level (p<0.05); in compared with diabetes mellitus induced group (DC), BUN levels of indigenous cinnamon powder hydrosol group (HP), low dosage cinnamon liquid extract group (EL), low dosage cinnamaldehyde nanoemulsion group (NL), high dosage cinnamon liquid extract group (EH), and high dosage cinnamaldehyde nanoemulsion group (NH) have a tendency of decreasing with the amounts of 30.41%, 35.04%, 39.68%, 48.96%, and 51.54%, respectively, all of which have significant difference (p<0.05), which indicates that indigenous cinnamon powder hydrosol group (HP), low dosage cinnamon liquid extract group (EL), low dosage cinnamaldehyde nanoemulsion group (NL), high dosage cinnamon liquid extract group (EH), and high dosage cinnamaldehyde nanoemulsion group (NH) are effective to reduce BUN level in blood, so as to reduce kidney damage for the sick diabetes mellitus mice, wherein the high dosage cinnamaldehyde nanoemulsion group (NH) has the best effect.

Creatinine (CREA) is break-down product of creatine phosphate in muscle tissue, which is one of the metabolic wastes excreted to urine by kidneys. When kidney dysfunction occurs, metabolism function is decreased, creatinine may accumulate in the blood rather than being excreted out of the body such that the concentration in the blood is increased. Thus, concentration of CREA in blood can be used for evaluating kidney function. According to table 8, in compared with normal control group (NC), diabetes mellitus induced group (DC) has a significantly higher CREA level (p<0.05); in compared with diabetes mellitus induced group (DC), CREA levels of indigenous cinnamon powder hydrosol group (HP), low dosage cinnamon liquid extract group (EL), low dosage cinnamaldehyde nanoemulsion group (NL), high dosage cinnamon liquid extract group (EH), and high dosage cinnamaldehyde nanoemulsion group (NH) have a tendency of decreasing with the amounts of 45.40%, 10.92%, 28.16%, 37.93%, and 39.66%, respectively, but all of which fail to reach significant difference (p>0.05).

In conclusion, after the above mentioned experiments, it is found that the composition for inhibiting diabetes mellitus of the present invention is more effective than the existed cinnamon powder intake, cinnamon hydrosol or cinnamon liquid extract for inhibiting diabetes mellitus, and more particularly, with the high dosage cinnamaldehyde nanoemulsion intake, the diabetes mellitus mice may have a weight gain of 31.12%, blood sugar reduction of 54.20%, significant improvement of glucose tolerance test (OGTT)

for oral glucose (p<0.05) to have the blood sugar level back to the original in 120 minutes after glucose intake, inhibiting 47.78% of high concentration insulin, reducing 75.95% of HOMA-IR index, reducing 32.93% of total cholesterol, 48.74% of triglyceride, 47.64% of aspartate aminotransferase, 46.88% of alanine aminotransferase, 13.79% of uric acid, 51.54% of blood urea nitrogen, and 39.66% of creatinine in blood, and thus the composition for inhibiting diabetes mellitus provided in the present invention does have the potential of being used as nutritional supplement for reducing blood sugar. In addition, the cinnamaldehyde nanoemulsion produced by using the specific method of manufacturing composition for diabetes mellitus in accordance with the present invention has the ingredients of the above mentioned composition for inhibiting diabetes mellitus, the cinnamaldehyde nanoemulsion can be actually used as the composition for inhibiting diabetes mellitus.

The foregoing descriptions are merely preferred embodiments of this disclosure, and do not constitute any limitation on this disclosure. Any form of variation such as equivalent replacement or modification made to the technical means and technical content disclosed in this disclosure without departing from the scope of the technical means of this disclosure is the content of the technical means of this disclosure and still falls within the protection scope of this disclosure.

What is claimed is:

1. A composition for inhibiting diabetes mellitus comprising 1 part by weight of soybean oil, 5 to 14 parts by weight of polysorbate-based emulsifier, 0.5 to 2 parts by weight of lecithin, 0.3 to 2 parts by weight of polyethylene glycol (PEG), 81 to 91 parts by weight of deionized water, and 2.345 to 17.833 parts by weight of cinnamaldehyde, wherein an average particle size of the composition for inhibiting diabetes mellitus is ranged between 33 nm to 37 nm, and a polydispersity index of the composition for inhibiting diabetes mellitus is ranged between 0.12 to 0.20.

2. The composition for inhibiting diabetes mellitus of claim 1, further comprising 0.14734 to 0.8813 parts by weight of cinnamic acid.

3. The composition for inhibiting diabetes mellitus of claim 1, further comprising 0.04122 to 0.4334 parts by weight of cinnamyl alcohol.

4. The composition for inhibiting diabetes mellitus of claim 1, further comprising 0.02504 to 0.0833 parts by weight of kaempferol.

5. The composition for inhibiting diabetes mellitus of claim 1, further comprising 0.0177 to 0.0947 parts by weight of benzoic acid.

6. The composition for inhibiting diabetes mellitus of claim 1, further comprising 0.0102 to 0.156 parts by weight of eugenol.

7. The composition for inhibiting diabetes mellitus of claim 1, further comprising 0.0037 to 0.0093 parts by weight of quercetin.

8. The composition for inhibiting diabetes mellitus of claim 1, further comprising 0.02504 to 0.0833 parts by weight of kaempferol-3-β-D-glucopyranoside.

9. The composition for inhibiting diabetes mellitus of claim 1, further comprising 0.0011 to 0.0067 parts by weight of rutin.

10. The composition for inhibiting diabetes mellitus of claim 1, further comprising 0.00108 to 0.00521 parts by weight of caffeic acid, 0.00086 to 0.0012 parts by weight of coumarin, 0.00038 to 0.0014 parts by weight of hyperoside and isoquercetin, 0.00080 to 0.001 parts by weight of p-coumaric acid, and 0.00012 to 0.0015 parts by weight of neochlorogenic acid.

\* \* \* \* \*